(12) United States Patent
Johnson, Jr. et al.

(10) Patent No.: US 10,983,117 B2
(45) Date of Patent: Apr. 20, 2021

(54) CARBON NANOTUBE BIOSENSORS AND RELATED METHODS

(75) Inventors: Alan T. Johnson, Jr., Philadelphia, PA (US); Mitchell Lerner, Philadelphia, PA (US); Matthew W. Robinson, Blue Bell, PA (US); Tatiana Pazina, St. Petersburg (RU); Dustin Brisson, Philadelphia, PA (US); Jennifer Dailey, Rockville, MD (US); Brett R. Goldsmith, Philadelphia, PA (US)

(73) Assignees: The Trustees of the University of Pennsylvania, Philadelphia, PA (US); The Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 14/241,671

(22) PCT Filed: Aug. 30, 2012

(86) PCT No.: PCT/US2012/053085
§ 371 (c)(1),
(2), (4) Date: Jul. 9, 2014

(87) PCT Pub. No.: WO2013/033359
PCT Pub. Date: Mar. 7, 2013

(65) Prior Publication Data
US 2015/0119263 A1    Apr. 30, 2015

Related U.S. Application Data

(60) Provisional application No. 61/529,341, filed on Aug. 31, 2011.

(51) Int. Cl.
*G01N 33/543* (2006.01)
*B82Y 30/00* (2011.01)
(Continued)

(52) U.S. Cl.
CPC ........ *G01N 33/54373* (2013.01); *B82Y 30/00* (2013.01); *G01N 33/54366* (2013.01);
(Continued)

(58) Field of Classification Search
None
See application file for complete search history.

(56) References Cited

U.S. PATENT DOCUMENTS 4,563,893 A   1/1986 Tanyolac et al.
5,369,028 A   11/1994 Harpold et al.
(Continued)

FOREIGN PATENT DOCUMENTS

WO    2010/014903 A1    2/2010
WO    WO 2012/050646    4/2012
WO    WO 2013/033359    3/2013

OTHER PUBLICATIONS

Lei et al., Nanotubes in Biosensing, Sep./Oct. 2010, Wiley Interdisciplinary Reviews: Nanomedicine and Nanobiotechnology, vol. 2, pp. 496-509.*
(Continued)

*Primary Examiner* — Melanie Brown
(74) *Attorney, Agent, or Firm* — BakerHostetler

(57) ABSTRACT

Disclosed are devices that comprise a protein, such as an antibody, placed into electronic communication with a semiconductor material, such as a carbon nanotube. The devices are useful in assessing the presence or concentration of analytes contacted to the devices, including the presence of markers for prostate cancer and Lyme disease.

20 Claims, 10 Drawing Sheets

(51) Int. Cl.
  *G01N 33/569* (2006.01)
  *G01N 33/574* (2006.01)
  *B82Y 15/00* (2011.01)
(52) U.S. Cl.
  CPC . *G01N 33/56911* (2013.01); *G01N 33/57415* (2013.01); *B82Y 15/00* (2013.01); *Y02A 50/30* (2018.01); *Y10S 977/746* (2013.01); *Y10S 977/92* (2013.01)

(56) References Cited

U.S. PATENT DOCUMENTS

| | | | |
|---|---|---|---|
| 6,493,638 | B1 | 12/2002 | McLean et al. |
| 6,649,403 | B1 | 11/2003 | McDevitt et al. |
| 6,905,655 | B2 | 6/2005 | Gabriel et al. |
| 7,129,554 | B2 | 10/2006 | Lieber et al. |
| 2003/0124572 | A1 | 7/2003 | Umek et al. |
| 2004/0007740 | A1* | 1/2004 | Abstreiter .......... G01N 27/4145 257/347 |
| 2004/0101851 | A1 | 5/2004 | White et al. |
| 2004/0200734 | A1 | 10/2004 | Co et al. |
| 2005/0051719 | A1 | 3/2005 | Miller et al. |
| 2006/0054936 | A1 | 3/2006 | Lieber et al. |
| 2006/0145194 | A1 | 7/2006 | Barron et al. |
| 2006/0240492 | A1* | 10/2006 | Rusling ................ G01N 33/551 435/7.23 |
| 2007/0292896 | A1 | 12/2007 | Strano et al. |
| 2008/0008760 | A1 | 1/2008 | Bianco et al. |
| 2008/0063566 | A1 | 3/2008 | Matsumoto et al. |
| 2008/0283875 | A1* | 11/2008 | Mukasa ................. B82Y 10/00 257/253 |
| 2009/0053212 | A1* | 2/2009 | Yamamoto ............. C07K 16/24 424/133.1 |
| 2009/0084678 | A1* | 4/2009 | Joshi .................. A61B 5/14532 204/403.14 |
| 2009/0090175 | A1 | 4/2009 | Shim et al. |
| 2009/0275066 | A1 | 11/2009 | Popot et al. |
| 2009/0280056 | A1* | 11/2009 | Dennis ............... A61K 47/6871 424/1.49 |
| 2010/0088040 | A1 | 4/2010 | Johnson, Jr. |
| 2010/0105082 | A1* | 4/2010 | Ramadurai .......... G01N 33/569 435/7.37 |
| 2010/0105834 | A1* | 4/2010 | Tour ....................... B82Y 30/00 525/50 |
| 2010/0112546 | A1 | 5/2010 | Lieber et al. |
| 2010/0176837 | A1 | 7/2010 | Kummel et al. |
| 2010/0184669 | A1* | 7/2010 | Harrison, Jr. .......... A61N 1/406 514/1.1 |
| 2010/0198521 | A1 | 8/2010 | Haick |
| 2010/0256344 | A1* | 10/2010 | Thompson ............. B82Y 10/00 534/558 |
| 2010/0270543 | A1* | 10/2010 | Choi ...................... B82Y 10/00 257/40 |
| 2011/0059871 | A1* | 3/2011 | Tour ....................... B82Y 30/00 507/137 |
| 2011/0098591 | A1 | 4/2011 | Haick et al. |
| 2013/0143247 | A1 | 6/2013 | Haick et al. |
| 2014/0015548 | A1 | 1/2014 | Naughton et al. |
| 2014/0155333 | A1* | 6/2014 | Harrison, Jr. .......... A61N 1/406 514/19.3 |
| 2016/0077047 | A1 | 3/2016 | Khamis et al. |

OTHER PUBLICATIONS

Bahr et al., Functionalization of Carbon Nanotubes by Electrochemical Reduction of Aryl Diazonium Salts: A Bucky Paper Electrode, 2001, J. Am. Chem. Soc., vol. 123, pp. 6536-6542.*
Mahouche-Chergui et al., Aryl diazonium salts: a new class of coupling agents for bonding polymers, biomacromolecules and nanoparticles to surfaces, 2011, Chem. Soc. Rev., vol. 40, pp. 4143-4166.*
Andriole et al, "Mortality Results From a Randomized Prostate-Cancer Screening Trial", N. Engl. J. Med., 2009, 360, 1310-9.
Burdo et al, "Osteopontin Prevents Monocyte Recirculation and Apoptosis", J. Leukocyte Bioi., 2007, 81, 1504-11.
Goldsmith, B.R. et al., "Biomimetic Chemical Sensors Using Nanoelectronic Readout of Olfactory Receptor Proteins", ACS Nano. Jun. 22, 2011, 5(7), 5408-5416.
Graff et al, "Synthesis of Nickel-Nitrilotriacetic Acid Coupled Single-Walled Carbon Nanotubes for Directed Self-Assembly With Polyhistidine-Tagged Proteins", Chern Mater., 2008, 20, 1824-9.
Ha et al. "Printed, Sub-3V Digital Circuits on Plastic From Aqueous Carbon Nanotube luk", ACS Nano Online ASAP, 2010.
Heller et al, "Identifying the Mechanism of Biosensing With Carbon Nanotube Transistors", Nano Lett., Feb. 2008, 8(2), 591-595.
Huang et al, "Immobilization of Antibodies and Bacterial Binding on Nanodiamond and Carbon Nanotubes for Biosensor Applications", Diamond Relat Mater. , Apr.-Aug. 2004, 3(4-8),I 098-I 02.
International Patent Application No. PCT/US12/53085: International Search Report and Written Opinion dated Jan. 25, 2013, 17 pages.
Khamis et al, "Optimized Photolithographic Fabrication Process for Carbon Nanotube Devices", AIP Advances, 2011, I, 022106.
Kim, S.N. et al, "Carbon Nanotubes for Electronic and Electrochemical Detection of Biomolecules", Adv. Mater., Oct. 19, 2007, 19(20), 3214-3228.
Lerner, M.B. et al, "Hybrids of a Genetically Engineered Antibody and a Carbon Nanotube Transistor for Detection of Prostate Cancer Biomarkers", ACS Nano., May 10, 2012, 6(6), 5143-5149.
Qi et al, "Toward Large Arrays of Multiplex Functionalized Carbon Nanotube Sensors for Highly Sensitive and Selective Molecular Detection", Nano Lett., Mar. 2003, 3(3), 347-5I.
Wikipedia.org. http://en.wikipedia.org/wiki/Langmuir eguation.
Zhang et al, "Functionalized Carbon Nanotubes for Detecting Viral Proteins", Nano Lett., 2007, 7(10), 3086-91.
Zheng, M. et al., "DNA-assisted dispersion and separation of carbon nanotubes," Nature Mater., 2003, 2, 338-342.
Zhang, D. et al., "Detection of $NO_2$ down to ppb Levels Using Individual and Multiple $In_2O_3$ Nanwire Devices," Nano Lett., 2004, 4, 1919-1924.
Wong et al., "Covalently Functionalized Nanotubes as Nanometer-Sized Probes in Chemistry and Biology," Nature, 2002, 420, 761.
Williams et al., "Carbon nanotubes with DNA recognition," Nature, 1998, 394, 52-55.
Wang, W. et al., "Label-free detection of small-molecule-protein interactions by using nanowire nanosensors," Proc. Natl. Acad. Sci. USA, 2005, 102, 3208-3212.
Valentini, L. et al., "Sensors for sub-ppm $NO_2$ gas detection based on carbon nanotube thin films," Appl. Phys. Lett., 2003, 82, 961-963.
Staii, C. et al., "High Frequency Scanning Gate Microscopy and Local Memory Effect of Carbon Nanotube Transistors," Nano Lett., 2005, 5(5), 893-896.
Staii, C. et al., "DNA-Decorated Carbon Nanotubes for Chemical Sensing," Nano Letters, 2005, 5(9), 1774-1778.
Snow, E.S. et al., "Chemical Detection with a Single-Walled Carbon Nanotube Capacitor," Science, 2005, 307, 1942-1945.
Sirdeshmuhk, R. et al., "Biological Functionalization of Carbon Nanotubes," Mat. Res. Soc. Symp. Proc., vol. 823.COPYRGT. 2004, Materials Research Society, W4.1.1-W4.1.6.
Sergi, M. et al., "Proteins, recognition networks and developing interfaces for macromolecular biosensing," J. Mol. Recog., 2004, 17, 198-208.
Radosavljevic, M. et al., "Nonvolatile Molecular Memory Elements Based on Ambipolar Nanotube Field Effect Transistors," Nano Lett., 2002, 2(7), 761-764.
Pengfei Qi et al., "Toward Large Arrays of Multiplex Functionalized Carbon Nanotube sensors for Highly Sensitive and Selective Molecular Detection," Nano Lett., 2003, 3, 347-351.
Patel, D.J. et al., "Structure, recognition and adaptive binding in RNA aptamer complexes," J. Mol. Biol., 1997, 272, 645-664.
Parrinello, M. et al., "Polymorphic transitions in single crystals: a new molecular dynamics method," J. Appl. Phys., 1981, 52, 7182-7190.
Novak, J.P. et al., "Nerve agent detection using networks of single-walled carbon nanotubes," Appl. Phys. Lett., 2003, 83, 4026-4028.

(56) References Cited

OTHER PUBLICATIONS

Nakao, H. et al., "Transfer-Printing of Highly Aligned DNA Nanowires," J. Am. Chem. Soc., 2003, 125(24), 7162-7163.

Martel, R. et al., "Single- and Multi-wall carbon nanotube field-effect transistors," Applied Physics Letters, Oct. 26, 1998, 73(17), 2447-2449.

Kong, J. et al., "Nanotube Molecular Wires as Chemical Sensors," Science, 2000, 287, 622-625.

Keren, K. et al., "DNA-Templated Carbon Nanotube Field-Effect Transistor", Science, 2003, vol. 302, pp. 1380-1382.

Hahm, J.I. et al., "Direct Ultrasensitive Electrical Detection of DNA and DNA Sequence Variations Using Nanowire Nanosensors," 2004, 4, 51-54.

Gouma, P. et al., "Novel Materials and Applications of Electronic Noses and Tongues," MRS Bulletin, Oct. 2004, 697-702.

Gelperin, A. et al., "Report No. FED003A03GELPE to U.S. Army Research Office", Jun. 8, 2010, pp. 1 -7.

Gelperin et al., "Nanotube-based sensor arrays for clinical breath analysis", J. Breath Res., Sep. 8, 2008, vol. 2, 037015, pp. 1 -6.

Gao, H. et al., "Stimulation of DNA-Nanotube Interactions," Annu. Rev. Mater. Res., 2004, 34, 123-150.

Freitag, M. et al., "Role of Single Defects in Electronic Transport through Carbon Nanotube Field-Effect Transistors," Phys. Rev. Lett., 2002, 89(21), 216801.

D'Amico, A. and Di Natale, C., "Electronic Nose Applications," Nose Summer School, Lloret de Mar, Oct. 2-6, 2000, University of Roma Tor Vergata.

Chopra, S. et al., "Selective gas detection using a carbon nanotube sensor", Appl. Phys. Lett., 2003, vol. 83, No. 11, p. 2280.

Chen, R.J. et al., "Noncovalent functionalization of carbon nanotubes for highly specific electronic biosensors," Proc. Natl. Acad. Sci. USA, 2003, 100, 4984-4989.

Chen, R.J. et al., "An Investigation of the Mechanisms of Electronic Sensing of Protein Adsorption on Carbon Nanotube Devices," J. Am. Chem. Soc., 2004, 126, 1563-1568.

Breaker, R.R., "Natural and engineered nucleic acids as tools to explore biology," Nature, 2004, 432, 838-845.

Bradley, K. et al., "Short-channel effects in contact-passivated nanotube chemical sensors," Appl. Phys. Lett., 2003, 3821-3823.

Bradley, K. et al., "Charge Transfer from Ammonia Physisorbed on Nanotubes," Phys. Rev. Lett., Nov. 2003, 91(21), 218301-1 to 218301-4.

Berendsen, H.J. et al., "Molecular dynamics with coupling to an external bath," J. Chem. Phys., 1984, 81, 3684-3690.

Barone, P.W. et al., "Near-infrared optical sensors based on single-walled carbon nanotubes," Nat. Mater., 2005, 4, 86-92.

Zuniga, C., et al., "Nanoenabled microelectromechanical sensor for volatile organic chemical detection", Applied Physics Letters, 2009. 94(22): p. 223122.

Zhou, X.J., et al., "Supported lipid bilayer/carbon nanotube hybrids", Nature Nanotechnology, 2007. 2(3): p. 185-190.

Zhang, Y.B., et al., Functionalized carbon nanotubes for detecting viral proteins. Nano Letters, 2007. 7(10): p. 3086-3091.

Zhang, X. M. et al., "High-throughput microarray detection of olfactory receptor gene expression in the mouse", Proceedings of the National Academy of Sciences of the United States of America 2004, 101, (39), 14168-14173.

Zhang et al., Coding of Sweet, Bitter, and Umami Tastes: Different Receptor Cells Sharing Similar Signaling Pathways, Feb. 7, 2003, Cell 112:293-301.

Yoon, H., et al., "Polypyrrole Nanotubes Conjugated with Human Olfactory Receptors: High-Performance Transducers for FET-Type Bioelectronic Noses", Angewandte Chemie-International Edition, 2009. 48(15): p. 2755-2758.

Xu, F.Q., et al., "Simultaneous activation of mouse main and accessory olfactory bulbs by odors or pheromones", Journal of Comparative Neurology, 2005. 489(4): p. 491-500.

Wise, P.M. et al., "Quantification of odor quality", Chemical Senses, 2000. 25(4): p. 429-443.

Wilson, D.A., "Habituation of odor responses in the rat anterior piriform cortex", Journal of Neurophysiology, 1998. 79(3): p. 1425-1440.

White, J., et al., "Solid-state, dye-labeled DNA detects volatile compounds in the vapor phase", Plos Biology, 2008. 6(1): p. 30-36.

Wasilko, D. J. et al., "The titerless infected-cells preservation and scale-up (TIPS) method for large-scale production of NO-sensitive human soluble guanylate cyclase (sGC) from insect cells infected with recombinant baculovirus", Protein Expression and Purification 2009, 65, (2), 122-132.

Uchida, N. and Z.F. Mainen, "Speed and accuracy of olfactory discrimination in the rat", Nature Neuroscience, 2003. 6(11): p. 1224-1229.

Tang, X. et al., "Carbon Nanotube DNA Sensor and Sensing Mechanism", Nano Letters 2006, 6, (8), 1632-1636.

Suwa et al., OR2AG1-Olfactory receptor 2AG1-*Homo sapiens*, Jul. 2001, UniProtKB-C9H205: 12 pages.

Sun, S.J., "Gas adsorption on a single walled carbon nanotube-model simulation", Physics Letters A, 2008. 372(19): p. 3493-3495.

Star, A., et al., Electronic detection of specific protein binding using nanotube FET devices. Nano Letters, 2003. 3(4): p. 459-463.

Staii, C. and AT. Johnson, "DNA-decorated carbon nanotubes for chemical sensing", Nano Letters, 2005. 5(9): p. 1774-1778.

Schwende, F.J. et al., "Volatile Compounds Associated with Estrus in Mouse Urine-Potential Pheromones", Experientia, 1984. 40(2): p. 213-214.

Saito, H. et al., "Odor Coding by a Mammalian Receptor Repertoire", Science Signaling, Nov. 2009, 2, (60), ra9.

Ritchie, T. K. et al., "Reconstitution of Membrane Proteins in Phospholipid Bilayer Nanodiscs", Methods in Enzymology; Liposomes, Pt F, 2009, 464, 211-231.

Repicky, S.E. and C.W. Luetje, "Molecular receptive range variation among mouse odorant receptors for aliphatic carboxylic acids", Journal of Neurochemistry, 2009, 109(1): p. 193-202.

Raming, K., et al., "Cloning and Expression of Odorant Receptors", Nature, 1993, 361(6410): p. 353-356.

Pevsner, J. et al., "Isolation and Characterization of an Olfactory Receptor Protein for Odorant Pyrazines", Proceedings of the National Academy of Sciences of the United States of America, 1985, 82, (9), 3050-3054.

Pengfei, Q.F., et al., "Toward large arrays of multiplex functionalized carbon nanotube sensors for highly sensitive and selective molecular detection", Nano Letters, 2003. 3(3): p. 347-351.

Peng, X.H. et al., "Functional Covalent Chemistry of Carbon Nanotube Surfaces", Advanced Materials, 2009, 21(6), 625-642.

Noy, A. et al., "Bionanoelectronics with 1D materials", Materials Today, 2009. 12(9): p. 22-31.

Nakanishi, S., Molecular Diversity of Glutamate Receptors and Implications for Brain Function, Oct. 23, 1992, Science 258:597-603.

Misra et al. Bioelectronic silicon nanowire devices using functional membrane proteins. PNAS. Aug. 18, 2009, vol. 106, No. 33, pp. 13780-13784.

McAlpine, M.C., et al., "Peptide-nanowire hybrid materials for selective sensing of small molecules", Journal of the American Chemical Society, 2008. 130(29): p. 9583-9589.

Lu, Y. et al., "DNA-decorated graphene chemical sensors", Applied Physics Letters, 2010, 97, (8), 083107.

Lee, T.M.H., "Over-the-counter biosensors: Past, present, and future", Sensors, 2008. 8(9): p. 5535-5559.

Kuang, Z.F., et al., "Biomimetic Chemosensor: Designing Peptide Recognition Elements for Surface Functionalization of Carbon Nanotube Field Effect Transistors", Acs Nano, 2010. 4(1): p. 452-458.

Kojima, A., et al., "Protein sensor using carbon nanotube field effect transistor", Japanese Journal of Applied Physics Part 1—Regular Papers Short Notes & Review Papers, 2005. 44(4A): p. 1596-1598.

Kim et al. Single-Carbon-Atomic-Resolution Detection of Odorant Molecules using a Human Olfactory Receptor-based Bioelectronic Nose. Adv. Mater. 2009, vol. 21, pp. 91-94.

Khalap, V.R., et al., "Hydrogen Sensing and Sensitivity of Palladium-Decorated Single-Walled Carbon Nanotubes with Defects", Nano Letters, 2010. 10(3): p. 896-901.

(56) References Cited

OTHER PUBLICATIONS

Khafizov, K., et al., "Ligand specificity of odorant receptors" Journal of Molecular Modeling, 2007. 13(3): p. 401-409.

Kajiya, K. et al., "Molecular bases of odor discrimination: Reconstitution of olfactory receptors that recognize overlapping sets of odorants", Journal of Neuroscience, 2001, 21, (16), 6018-6025.

Guo, X., et al., "Covalently bridging gaps in single-walled carbon nanotubes with conducting molecules", Science, 2006. 311: p. 356-9.

Goldsmith, B.R., et al., "Conductance-controlled point functionalization of single-walled carbon nanotubes", Science, 2007. 315(5808): p. 77-81.

Goldsmith et al. "Biomimetic Chemical Sensors Using Nanoelectronic Readout of Olfactory Receptor Proteins." ACS Nano. Jun. 22, 2011, vol. 5, No. 7, pp. 5408-5416.

Furton, K.G. and L.J. Myers, "The scientific foundation and efficacy of the use of canines as chemical detectors for explosives", Talanta, 2001. 54(3): p. 487-500.

Filmore, D., "It's a GPCR World", Modern Drug Discovery, 2004. 7(11): p. 24-28.

Duchamp-Viret, P. et al., "Odor response properties of rat olfactory receptor neurons", Science, 1999. 284(5423): p. 2171-2174.

Denisov, I. G. et al., "Directed self-assembly of monodisperse phospholipid bilayer nanodiscs with controlled size", Journal of the American Chemical Society 2004, 126, (11), 3477-3487.

Dan, Y.P., et al., "Intrinsic Response of Graphene Vapor Sensors", Nano Letters, 2009. 9(4): p. 1472-1475.

D.J. Wasilko and S.E. Lee "TIPS: Titerless Infected-Cells Preservation and Scale-up" (2006), Bioprocessing Journal, 29-32 [Abstract only].

Collins, P.G., et al., "Extreme oxygen sensitivity of electronic properties of carbon nanotubes", Science, 2000. 287(5459): p. 1801-1804.

Christophe, C., et al., "Rats for demining: an overview of the APOPO program", Proceedings of the Eudem Conference on humanitarian landmine detection technologies, 2004.

Chen, R. J. et al., "Noncovalent functionalization of carbon nanotubes for highly specific electronic biosensors", Proceedings of the National Academy of Sciences of the United States of America, 2003, 100, (9), 4984-4989.

Breer, H., "Olfactory receptors: molecular basis for recognition and discrimination of odors", Analytical and Bioanalytical Chemistry, 2003. 377(3): p. 427-433.

Bradley, K., et al., "Integration of cell membranes and nanotube transistors", Nano Letters, 2005. 5(5): p. 841-845.

Bayburt, T.H. and S.G. Sligar, "Self-assembly of single integral membrane proteins into soluble nanoscale phospholipid bilayers", Protein Science, 2003. 12(11): p. 2476-2481.

Bayburt, T.H. and S.G. Sligar, "Membrane protein assembly into Nanodiscs", Febs Letters, 2010. 584(9): p. 1721-1727.

Bayburt, T. H. et al., "Self-assembly of discoidal phospholipid bilayer nanoparticles with membrane scaffold proteins", Nano Letters 2002, 2, (8), 853-856.

Bahr, J.L., et al., "Functionalization of carbon nanotubes by electrochemical reduction of aryl diazonium salts: A bucky paper electrode", Journal of the American Chemical Society, 2001. 123(27): p. 6536-6542.

Azpiazu, I. and N. Gautam, "A fluorescence resonance energy transfer-based sensor indicates that receptor access to a G protein is unrestricted in a living mammalian cell", Journal of Biological Chemistry, 2004. 279(26): p. 27709-27718.

Albert, K.J., et al., "Cross-reactive chemical sensor arrays", Chemical Reviews, 2000. 100(7): p. 2595-2626.

Akimov, V., et al., "Nanobiosensors based on individual olfactory receptors", Analog Integrated Circuits and Signal Processing, 2008. 57(3): p. 197-203.

Abaffy, T. et al., "Functional analysis of a mammalian odorant receptor subfamily", Journal of Neurochemistry, 2006, 97, (5), 1506-1518.

Agarwal et al., Immobilization of Histidine-Tagged Proteins on Nickel by Electrochemical Dip Pen Nanolithography, Dec. 20, 2002, J. Am. Chem. Soc. 125:7408-7412 (Year: 2002).

* cited by examiner

CARBON NANOTUBE BIOSENSORS AND RELATED METHODS

CROSS-REFERENCE TO RELATED APPLICATIONS

This application is the National Stage of International Application No. PCT/US2012/053085, filed Aug. 30, 2012, which claims the benefit of U.S. Provisional Application No. 61/529,341, filed Aug. 31, 2011, the entireties of which are incorporated herein by reference for any and all purposes.

STATEMENT OF GOVERNMENT INTEREST

This invention was made with government support under grant number W81XWH-09-1-0206 awarded by the Army/Medical Research and Material Command Office. The government has certain rights in the invention.

TECHNICAL FIELD

The present disclosure relates to the field of carbon nanotubes and to the field of conjugating biomolecules to electronic devices.

BACKGROUND

Carbon nanotubes have attracted attention because of their electrical, mechanical, and optical properties. Carbon nanotube field effect transistors (CNTFETs) provide a unique platform for biosensing applications. Since every atom is on the surface, carbon nanotubes are sensitive to small changes in their immediate surroundings.

Cancer detection is one application of sensors. Prostate cancer represents a major public health issue as the most commonly diagnosed cancer and third leading cause of cancer deaths among American men. Detection of early-stage cancer often results in successful treatment, with long term disease-free survival in 60-90% of patients.

One particular methodology for early disease diagnosis and to guide therapy selection is biomarker detection. Biomarkers of cancer are molecular or tissue-based signatures of disease that can be detected through specialized assays and provide insight into disease etiology or progression. Osteopontin (OPN) is a potential new biomarker for prostate cancer. OPN exhibits a diverse functionality in immunity, infection, and cancer progression; specifically, osteopontin prevents cell apoptosis. Traditional biomarker detection methods such as ELISA are sensitive, but require pure samples, lengthy processing times, expertise in molecular biology and could be expensive. Immunosensors capable of the same or improved sensitivity compared to an ELISA assay that can improve on one or several of these aspects would be preferable to existing technologies.

SUMMARY

In meeting the described challenges, the present disclosure provides devices, the devices comprising a semiconductor; a protein coupled to the semiconductor such that the protein is in electronic communication with the semiconductor; and a detector device capable of detecting a change in an electronic characteristic of the protein related to an interaction between the protein and an analyte complementary to the protein.

The disclosure also provides methods of fabricating sensors, the methods comprising coupling a protein to a semiconductor so as to place the protein into electronic communication with the semiconductor.

The disclosure further provides methods of assaying a sample, the methods including contacting a sample with a device comprising a protein in electronic communication with a semiconductor material in electronic communication with the protein; and measuring a first electronic characteristic of the device when the device is contacted with the sample.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
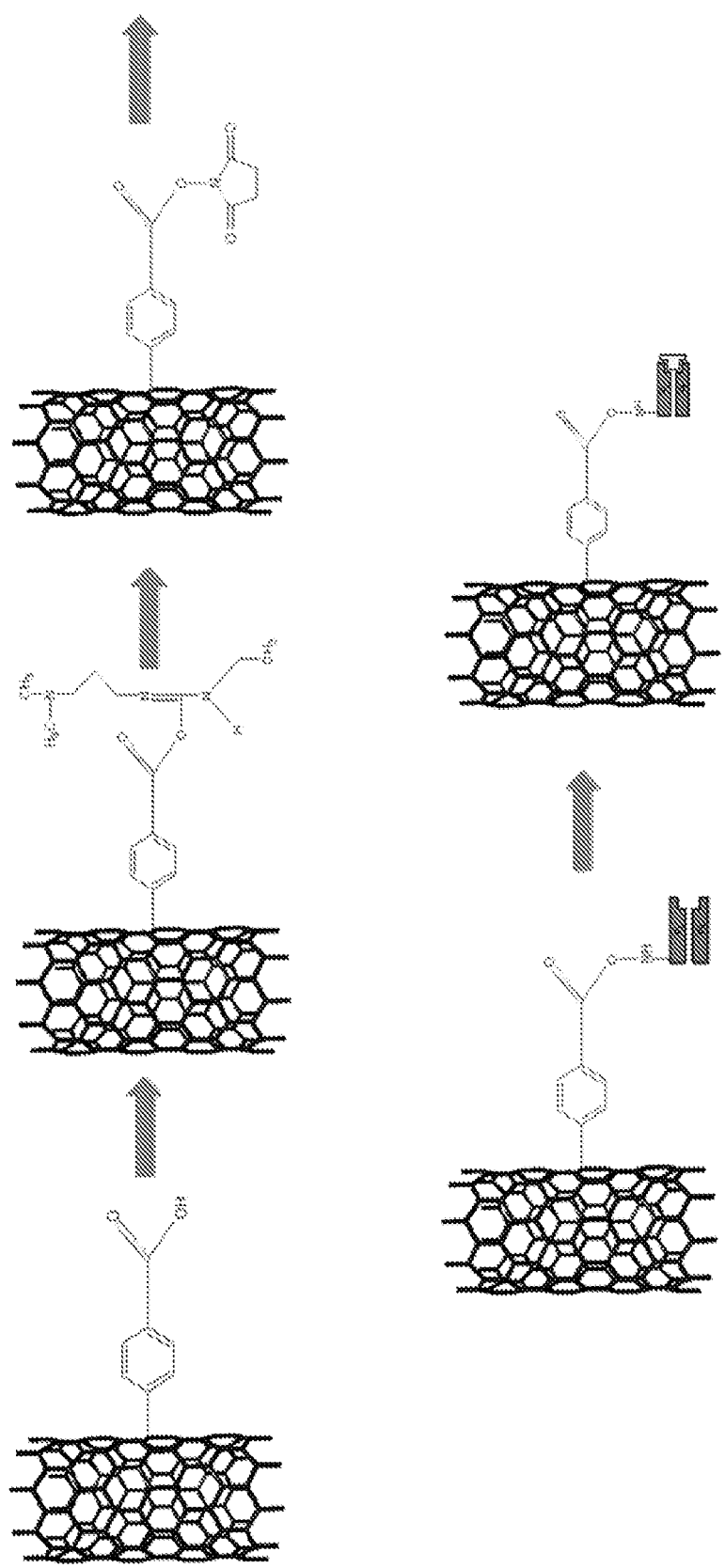
FIG. 1 illustrates an exemplary functionalization scheme for OPN attachment. First, the nanotube sidewall is functionalized through the use of a diazonium salt. The carboxylate group is then activated by EDC and stabilized with NHS. ScFv protein displaces the NHS to form an amide bond, and OPN binds preferentially to the ScFv in the detection step.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range. Any and all documents cited in this application are incorporated herein by reference in their entireties.

In one aspect, the present disclosure provides devices, which devices are suitable for use as sensors. The devices suitably include a semiconductor; a protein coupled to the semiconductor such that the protein is in electronic communication with the semiconductor; and a detector device capable of detecting a change in an electronic characteristic of the protein related to an interaction between the protein and an analyte complementary to the protein.

Changes in electrical characteristics can be measured using conventional electronic instrumentation that is operated manually or under computer control. For example, a computerized laboratory set up might include a National Instrument PCI-6722 DAQ board to apply the bias voltage and various values of gate voltage. A Keithley 6485 Picoammeter could then be used to measure current, providing a full I-Vg curve. In the case where one wished to measure many devices located on a single substrate, a switching matrix (Keithley 7001) or other multiplexer could be used. With suitable redesign, the complete measurement electronic system could be incorporated into a small, and relatively inexpensive unit that could be located at a point-of-care facility and operated by someone with minimal training.

Carbon nanotubes are considered especially suitable semiconductor materials. Materials that include silicon are also suitable. Single-wall, multi-wall (including double-wall) carbon nanotubes are all considered suitable. Nanotubes may be purchased commercially or grown according to the user's needs. A variety of methods of growing carbon nanotubes will be known to those of ordinary skill in the art; such methods include arc discharge, laser ablation, high pressure carbon monoxide (HiPCO), and chemical vapor deposition.

A variety of proteins are suitably coupled to the semiconducting material. It should be understood that the protein need not be coupled directly to the semiconducting material, as one or more atoms or other molecules may be present between the protein and the semiconducting material. This is shown in exemplary FIG. 1. A protein may be an antibody, a transmembrane protein, a G protein, a membrane protein, an enzyme, a receptor, a lectin, or some combination of these. It should be understood that multiple proteins may be coupled to a given semiconductor. For example, an antibody complementary to antigen 1 and an antibody complementary to antigen 2 may be coupled to the same carbon nanotube.

Alternatively, the devices may include multiple, individually addressable semiconductors that are coupled to different proteins. For example, a device might include ten individually addressable carbon nanotubes, each of which is coupled to a different protein complementary to a different analyte. In this way, the user may construct a multiplexed device that is sensitive to multiple analytes. Such multiplexed devices may include tens, hundreds, or even thousands of semiconductors. A device may include two or more semiconductors that are coupled to the same kind of protein so as to introduce a double-check into the device. For example, a device might include two nanotubes, each of which is bound (separately) to an antibody complementary to antigen 1.

Where the protein is an antibody, the user may use a single-chain variable fragment antibody. One such suitable antibody is a scFv antibody that has a high binding affinity for osteopontin. Other antibodies are suitable, including antibodies that are complementary to cancer biomarkers, such as carcinoembryonic antigen, or even prostate specific antigen.

Figure 10:
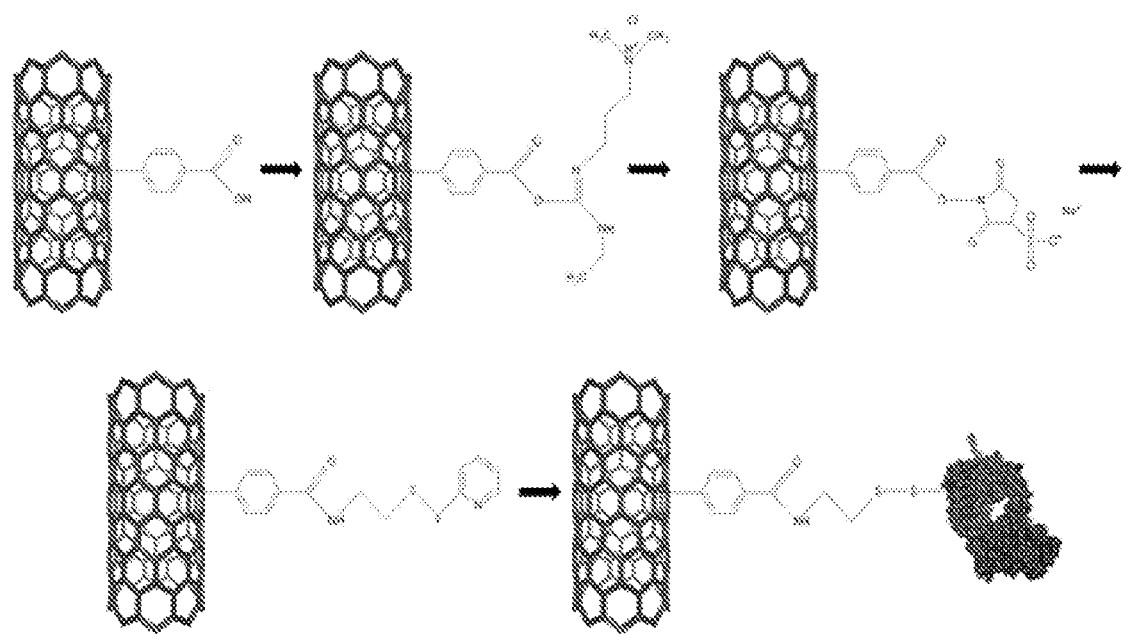
FIG. 10 illustrates an exemplary attachment between a protein and a nanotube using a cysteine chemistry according to the present disclosure.

Proteins suitable for use in the present devices may also include an amine group, a histidine tag, or some other functionalization (including a cysteine residue, as described elsewhere herein) used to couple the protein to the semiconductor. In the case of a protein having an amine group, the user may use the amine group to displace a leaving group coupled to the semiconductor so as to bind the protein to the semiconductor. The coupling need not necessarily be accomplished by a nucleophile-leaving group reaction, as coupling may occur by covalent bond (e.g., an amide bond), an ionic bond, by hydrogen bonding, or by metallic coordination. As one example of coordination, the protein may be coupled to the semiconductor by coordination between a histidine tag and nickel. A protein may also, as described herein, be coupled to the semiconductor by way of a cysteine residue (e.g., FIG. 10). In some embodiments, the protein to be attached naturally includes a cysteine residue. This could be naturally occurring or such a residue could be intentionally incorporated into a natural or recombinant protein. Further information may be found in patent application PCT/US2011/042290, "Biomimetic Chemical Sensors Using Nanoelectronic Readout Of Olfactory Receptors," filed Jun. 29, 2011, the entirety of which is incorporated herein by reference.

Also provided herein are methods of fabricating sensors. These methods suitably include coupling a protein to a semiconductor so as to place the protein into electronic communication with the semiconductor.

One exemplary coupling process is shown in FIG. 1. As shown in that figure, the user may functionalize a nanotube sidewall through the use of a diazonium salt. The carboxylate carboxylate group is then activated by EDC and stabilized with NHS. A ScFv protein displaces the NHS to form an amide bond, and OPN binds preferentially to the ScFv in the detection step.

The protein is suitably maintained in essentially its natural configuration following coupling to the semiconductor. In this way, the protein's natural analyte-binding characteristics are preserved in the assembled device.

As described elsewhere herein, carbon nanotubes are considered especially suitable semiconductors. Materials that include silicon are also considered suitable.

The coupling may be effected by displacing a leaving group coupled to the semiconductor with an nucleophile group of the protein so as to form a bond that places the protein in electronic communication with the semiconductor. A variety of moieties are considered suitable leaving groups; in one embodiment, the leaving group comprises N-Hydroxysuccinimide and the nucleophile comprises an amine group. The amine group is suitably part of the protein. In alternative embodiments, however, the leaving group may be present on the protein, and the nucleophile or displacing moiety is present on the carbon nanotube. In one illustrative embodiment, the user may coordinate a histidine residue on the protein with nickel coupled to the semiconductor.

In another embodiment, the present disclosure provides devices, comprising a semiconductor and a protein coupled to the semiconductor with a linkage comprising a cysteine residue such that the protein is in electronic communication with the semiconductor. The device may also include a detector device capable of detecting a change in an electronic characteristic of the protein related to an interaction between the protein and an analyte complementary to the protein. The semiconductor may be a carbon nanotube (single, double, or multiwall). A variety of suitable proteins are described herein; one exemplary protein is an antibody to Lyme flagellar protein or even Lyme flagellar protein itself. The foregoing exemplary chemistries are not limiting of the present disclosure, as a variety of other chemistries may be used to link a protein to the semiconductor, including amide bonds, imide bonds, and the like.

It should be understood that the presently disclosed articles and methods are not limited to complete proteins, as portions of proteins (e.g., binding regions) may also be used. Natural and recombinant proteins are also both suitable for the disclosed technologies.

Further disclosed are methods of assaying a sample. These methods include contacting a sample with a device comprising a protein in electronic communication with a semiconductor material in electronic communication with the protein; and measuring an electronic characteristic of the device when the device is contacted with the sample.

The electronic characteristic may be a conductivity, a resistance, a current, a voltage, or some combination of these. The user may compare the electronic characteristic of the device to a corresponding electronic characteristic measured when the device is exposed to a control, a known analyte, or both. For example, the user may compare the current or conductivity observed when a device is contacted to a sample to the corresponding current or conductivity observed when a device is contacted to a control. The user may also generate an estimate of the presence of one or more analytes in the sample. This may be accomplished by comparing the electronic characteristic observed in a sample (e.g., current, conductivity) to a calibration curve of that characteristic that corresponds to data points gathered from a control or standard having a known amount of an analyte of interest. In this way, the user may estimate the concentration of an analyte present in a sample to which the device has been contacted.

The user may construct a library of one or more electronic characteristics of the device that correspond to the device's exposure to one or more known analytes. For example, a user may construct a library of results that represents the current, conductivities, or other characteristics observed when a device is exposed to various concentrations of analytes.

Exemplary Fabrication Process

An exemplary process for fabricating CNTFET-protein hybrid devices is set forth below. First, carbon nanotubes are grown on an oxidized silicon wafer by chemical vapor deposition, using well known methods. Alternatively, nanotubes are deposited or printed from solution; semiconducting carbon nanotubes are considered especially suitable.

Electrical contacts are made using a photolithographic and sample cleaning process. A method of chemically functionalizing nanotubes is shown in FIG. 1.

As shown in that figure, the NT transistor is functionalized by incubation at 40° C. in a water solution of carboxylateddiazonium salt (2.5 mg/mL in DI water). Carboxylic acid groups from the diazonium functionalization are activated and stabilized with 1-ethyl-3-[3-dimethylaminopropyl]carbodiimide hydrochloride/sulfo-Nhydroxysuccinimide (EDC/NHS) at an EDC concentration of 16 mg/15 mL MES buffer and NHS concentration of 6 mg/15 mL MES buffer. NHS molecules are displaced by scFv proteins (11 tg/mL) in standard PBS buffer, forming a covalent amide bond between the protein and the carbon nanotube. The devices were then electrically characterized and are ready to be used as OPN biosensors.

Figure 2:
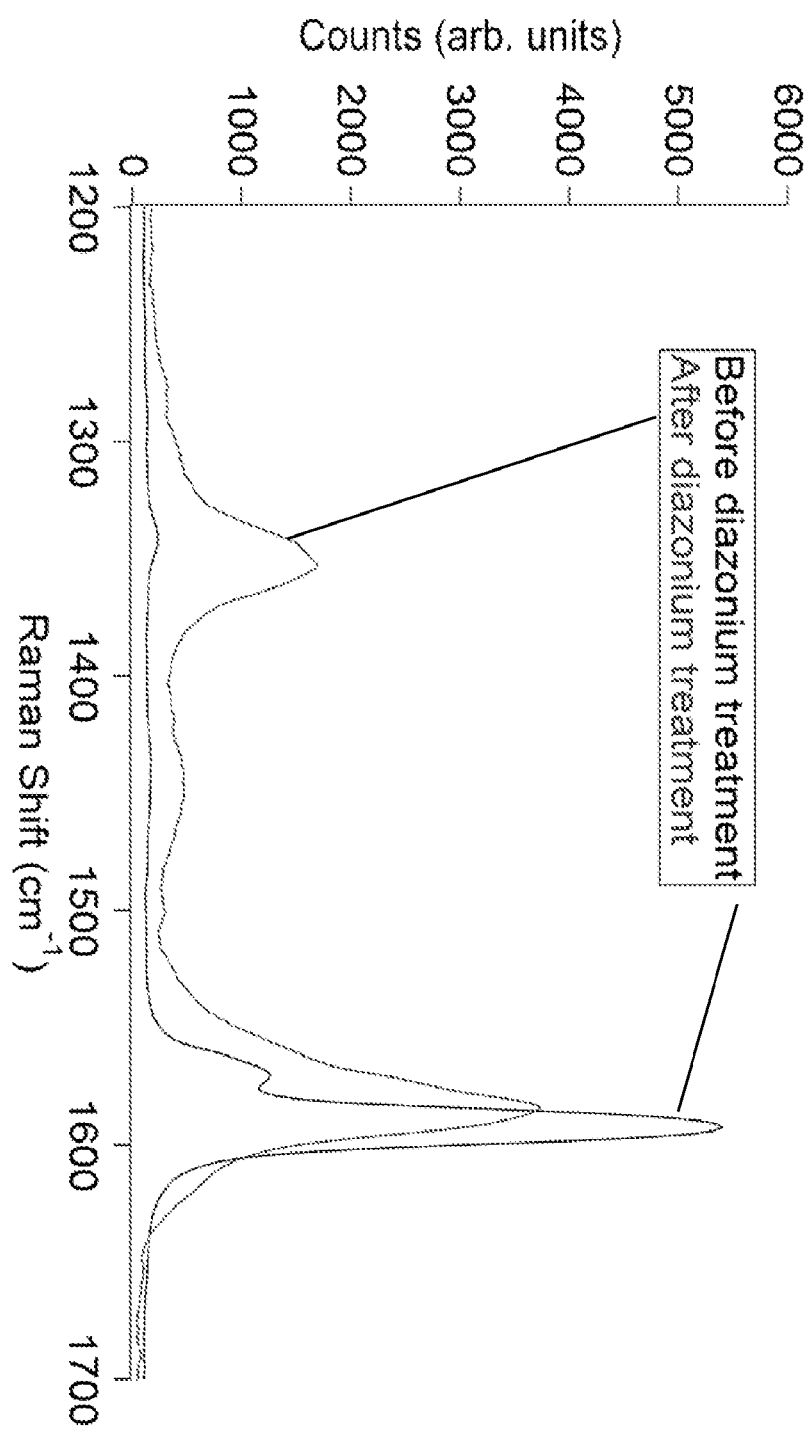
FIG. 2 presents Raman spectra of carbon nanotubes before and after exposure to a diazonium salt solution. The presence of a strongly enhanced D-band near 1360 cm after diazonium treatment indicates the formation of numerous carboxy-benzene sites on the nanotube sidewall.

The efficacy of the functionalization procedure may be been demonstrated through the use of Raman spectroscopy, Atomic Force Microscopy, and electronic transport measurements. A comparison of Raman spectra (FIG. 2) of as-grown carbon nanotubes and the same sample after incubation in the diazonium salt solution shows a strongly increased D ("disorder") peak at appx. 1360/cm in the latter, consistent with the formation of carboxylic groups as assumed for the chemical functionalization procedure in FIG. 1.

Figure 3:
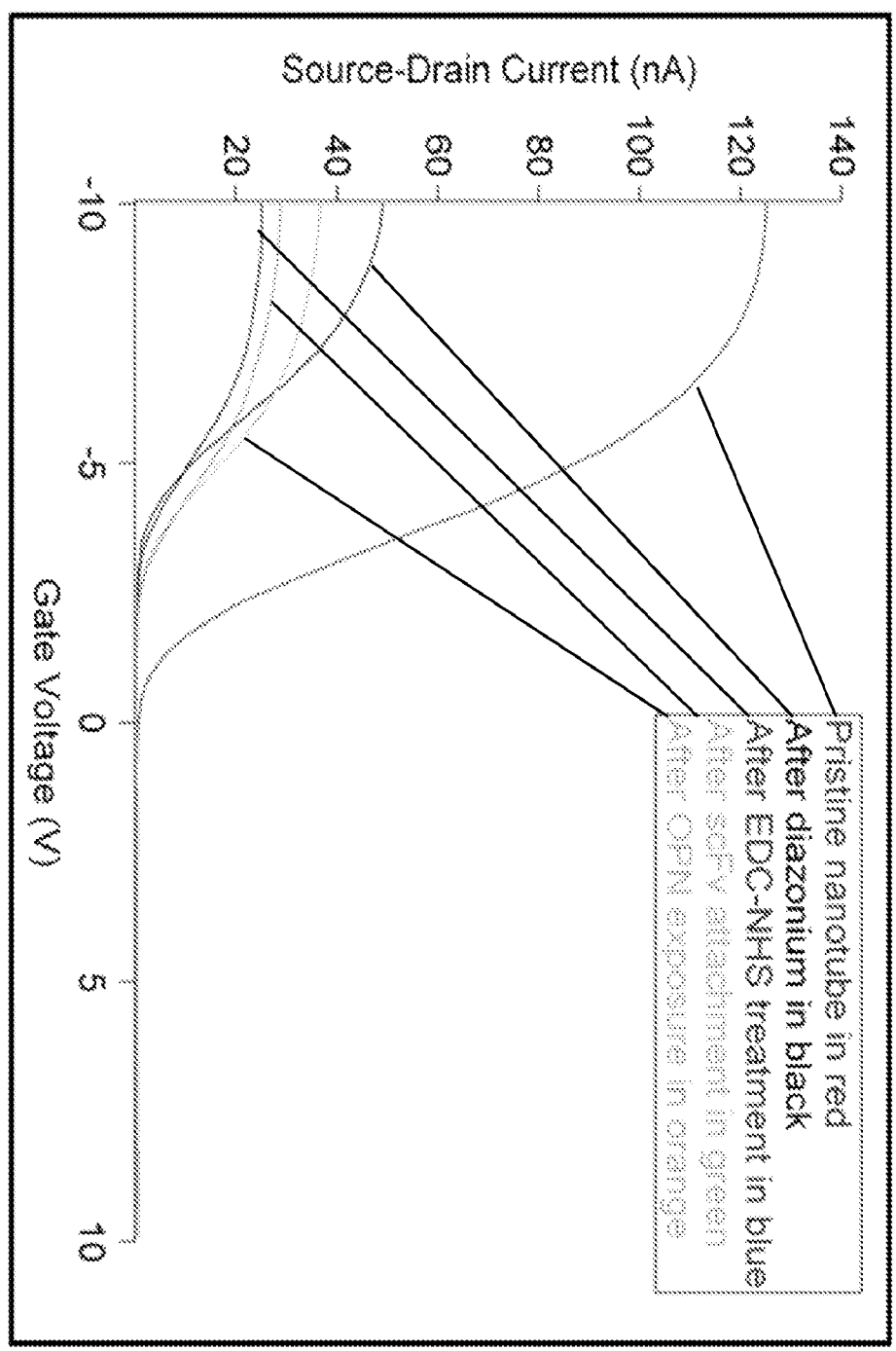
FIG. 3 illustrates I-Vg plots in forward gate sweep after successive functionalization steps. Note the ON state current increases following exposure to a solution of 100 ng/ml, OPN in PBS buffer.
Figure 4:
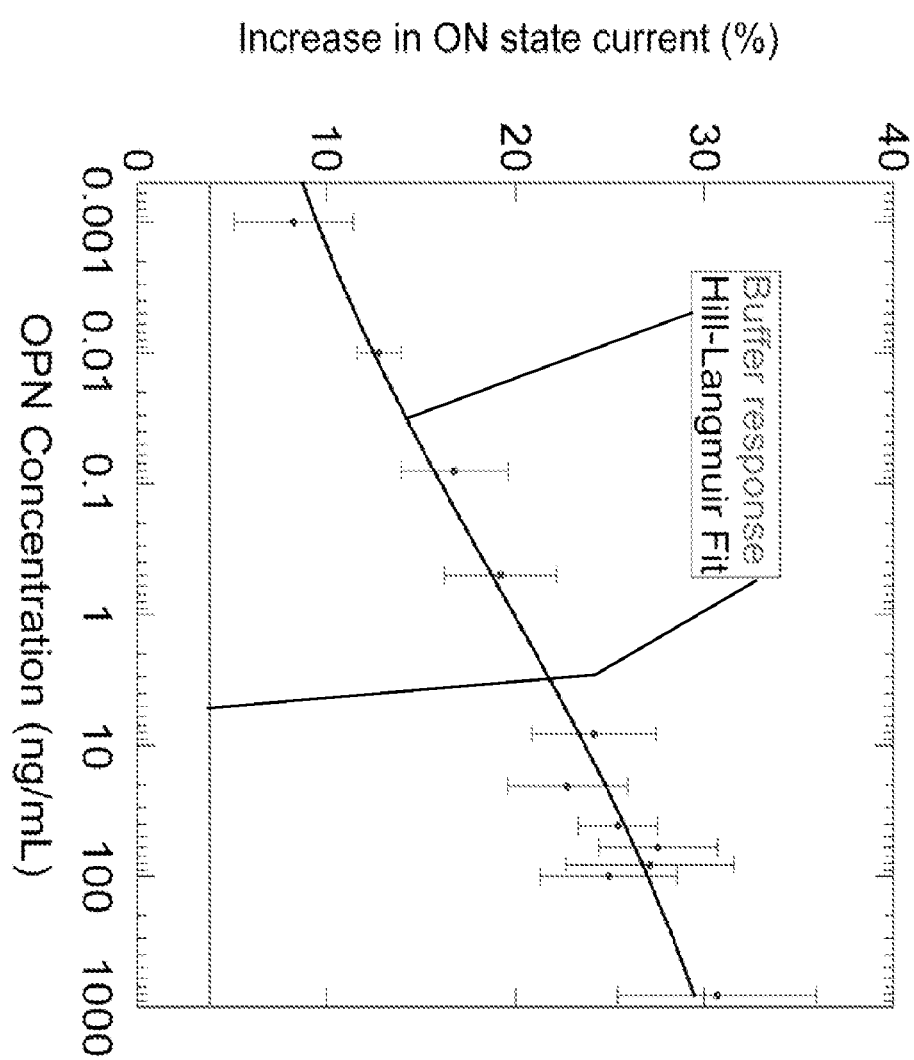
FIG. 4 illustrates a sensor response (increase in source-drain current) versus OPN concentration. The signal is still discernable from the bare buffer response at 1 pg/ml, OPN.

ScFv-functionalized devices exposed to osteopontin show an increase in the source-drain conductance of the carbon nanotube transistor that is a function of the osteopontin concentration, as evidenced by the electrical data shown in FIG. 3. This percentage increase in source-drain current is defined as the sensing response. The sensor responses have been measured down to 1 pg/mL of OPN in PBS buffer. One can observe excellent agreement with the Langmuir-Hill theory of ligand-receptor binding, with an scFv affinity of approximately 500 pg/mL. FIG. 4 shows the experimental data fit to the Hill equation, modified with an offset to account for the small sensor response to buffer alone and an overall scale factor.

Figure 5:
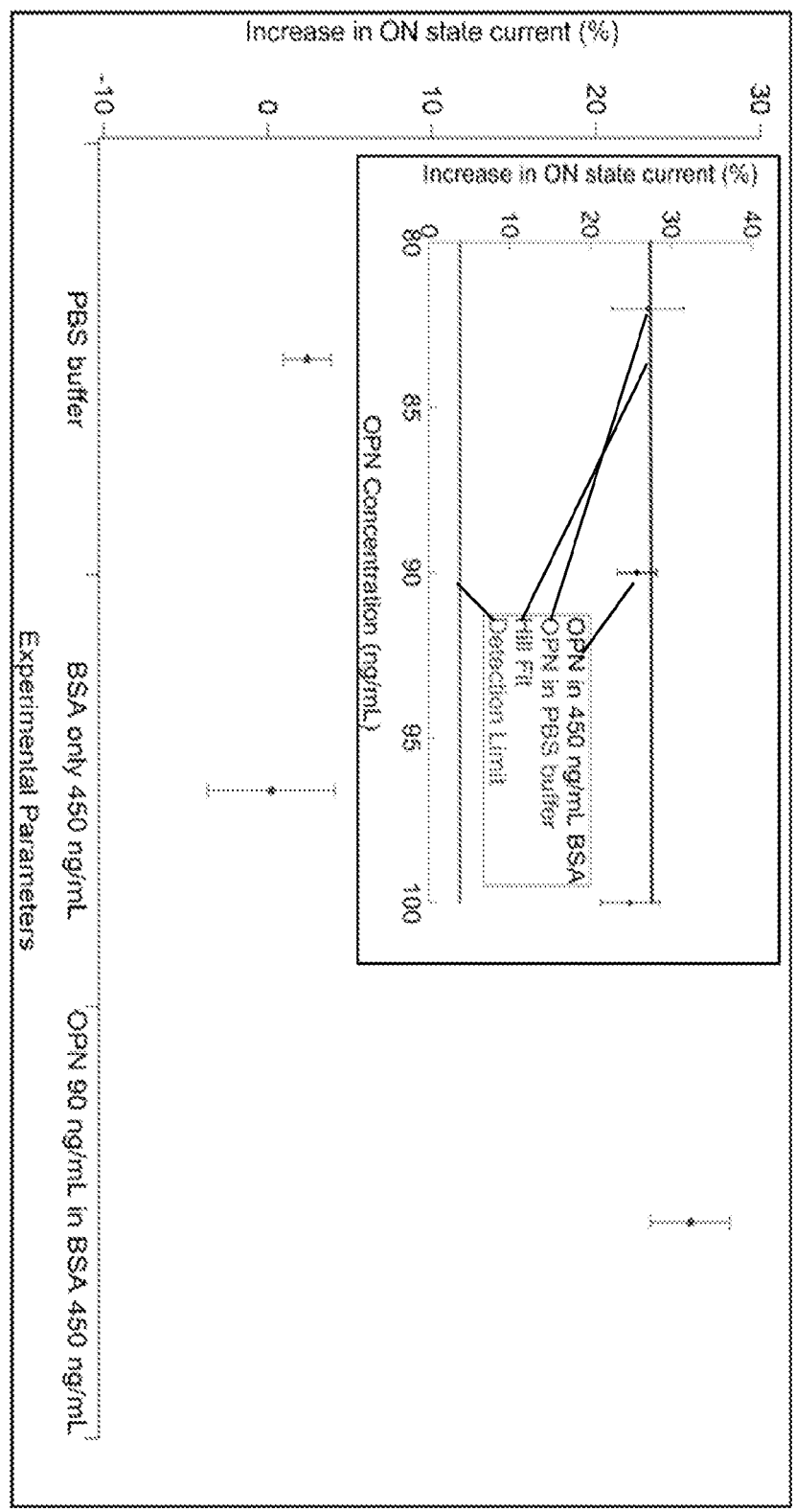
FIG. 5 illustrates sensor response (percentage increase in source-drain current) for buffer without protein BSA protein in buffer, and OPN-BSA 1:5 mixture in buffer. Bare buffer and BSA alone show no response, but the signal for the OPN/BSA mixed sample falls within one standard deviation of the Hill fit.
Figure 6:
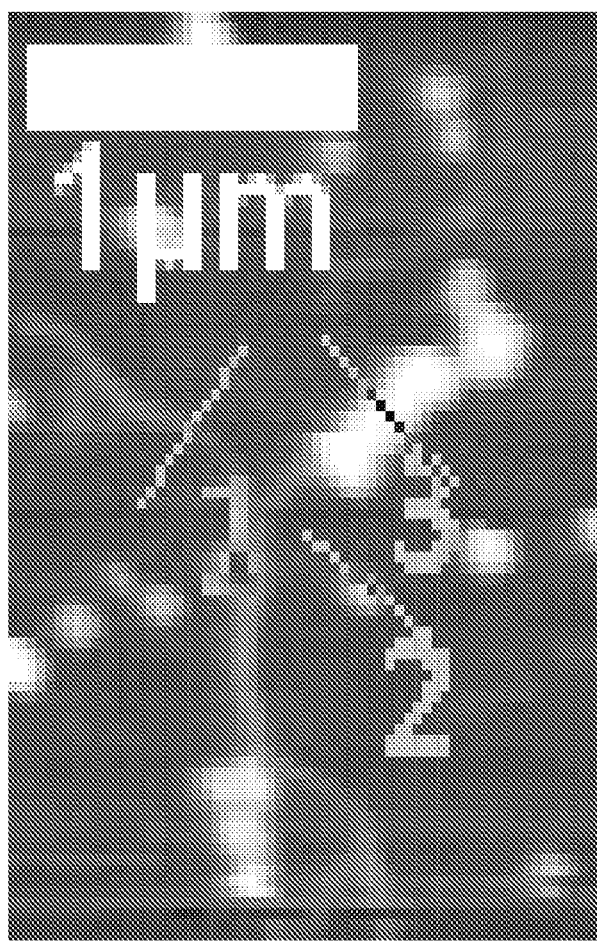
FIG. 6 illustrates Atomic Force Microscope image of synthetic Mu receptor proteins attached to carbon nanotubes via cysteine chemistry.

The anti-OPNscFv has been engineered to specifically bind OPN. Biosensor specificity was tested using large concentrations of bovine serum albumin (BSA) protein as a negative control. The response of the biosensor to BSA in buffer at 450 ng/mL is identical to its response to pure buffer, indicating that sensor response is specific to OPN. Moreover, demonstrating its suitability for use in detection of OPN in complex media (e.g., serum), the biosensor response to a mixture of OPN and BSA at 90 ng/mL and 450 ng/mL in PBS buffer is identical to the response to a solution of OPN at 90 ng/mL. Thus, even in a background five times more dense with interfering, non-targeted BSA protein, covalently functionalized CNTFETs can detect OPN with no loss of sensitivity. These experiments are summarized in FIG. 5.

Without being bound to any single theory, the mechanism for this sensing response is presumed to be decreased electronic scattering upon OPN binding due to compensation of charged sites on the anti-OPNscFv.

Comparison with Existing Technologies

Conventional tests for the presence of an antigen rely on enzyme-linked immunosorbantassay (ELISA) tests. The electronic readout of protein binding provides many advantages over this technology.

ELISA techniques require expertise in molecular biology and are performed by first immobilizing an unknown amount of antigen on a substrate. Detection antibodies with an affinity for the unknown antigen are added; these antibodies are pre-labeled with an enzyme through a bioconjugation process. A substrate for the enzyme is applied and catalysis by the enzyme leads to a color change in the sample. Rapidity and strength of the color change are proportional to the amount of enzyme, which is equal to the amount of detection antibody, which is proportional to the initial amount of antigen. Therefore, the qualities of the color change are taken as the sensing response. This technique is limited by the arbitrariness of the cutoff between positive and negative response as well as long incubation times and detection limits of order 1 ng/mL. CNTFET-based detection offers significantly lower, quantifiable detection limits as well as fast, all-electronic readout that can be performed by any technician in a point-of-care diagnostic setting.

The above examples are illustrative only, as the approach can be generalized to detection of any proteinaceous biomarker through the use of a suitably sensitive scFv.

As explained above, a protein may be bound to a nanotube by, e.g., formation of an amide bond to an exterior residue with an exposed amine group, or formation of a bond to the histidine tag of a recombinant protein using nickel-nitrilotriacetic acid (Ni-NTA) chemistry. An additional, alternative method for precise control over the attachment point is also provided. This method uses a chemistry path that enables formation of a bond to a cysteine residue.

Cysteine residues are found in nature; there are generally only one or two such residues in a given protein. Moreover, a cysteine residue that was engineered into a recombinant protein may, in some cases, result in only a minor modification. An attachment chemistry aimed at cysteine binding has a defined anchor point on the protein, as there is likely to be only one cysteine available. By anchoring the protein attachment at a known site, it can be assured that the epitope will remain unobstructed.

Figure 8:
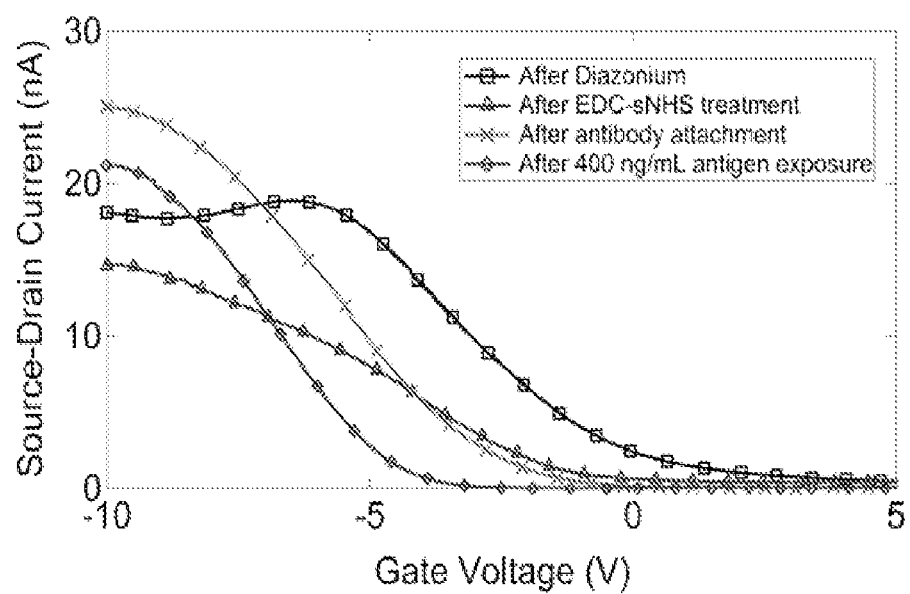
FIG. 8 illustrates a series of I-Vg curves during functionalization showing the effects of antigen exposure.

An exemplary cysteine functionalization proceeds as follows:

1) Create sp3 hybridized sites on the carbon nanotube. This may be accomplished by using diazonium oxidation with 4-carboxybenzene diazonium tetrafluoroborate. The user may, for example, incubate a nanotube chip in a solution of 2.2 mg diazonium salt/mL DI water in a water bath at 40° C. for 1 hour. The user may then dip the chip in an acetone bath for 1 min, transfer to a methanol bath for 1 min, then a DI water bath for 1 min.

2) Activate and stabilize the attachment sites. This may be accomplished with EDC and sulfo-NHS. From the example above, a use may place the chip from the last DI water bath into a beaker containing 16 mg sulfo-NHS and 6 mg EDC per 15 mL MES buffer. Reacts 15 mins at room temperature. When finished, rinse in DI water bath for 1 min.

3) Introduce a reactive disulfide group. This may be done with, e.g., PDEA (purchased commercially). Place the chip from the last DI water bath into a solution of 2 mM 2-(2-pyridinyldithio)ethaneamine hydrochloride (PDEA) in borate buffered saline (BBS buffer) and react 30 mins Rinse in DI water bath 1 min. Dry with nitrogen.

4) Pipet 1 ug/mL antibody-containing solution onto the nanotube chip and let sit 1 hour in a humid environment to prevent the droplet from drying out. The disulfide group from the PDEA will split and the cysteine residue in the target protein with bind to the free sulfur. Rinse in 2 DI water baths for 1 min each and blow dry under gentle nitrogen.

The validity of this attachment chemistry has been confirmed by atomic force microscopy (AFM). FIG. 6 is an AFM image showing proteins attached to the carbon nanotubes using the cysteine chemistry. Recombinant proteins with a single cysteine residue were used for these experiments.

The disclosed attachment chemistry applies to a wide class of antibodies. This has been verified by applying it to different antibody molecules. One example used a second scFv antibody called anti-HER2 4D5, which binds a protein indicative of breast cancer. Following the same procedures described herein for the binding of anti-OPN 23C3 scFv, one could successfully attach anti-HER2 4D5 scFv as confirmed by atomic force microscopy (see FIG. 7).

One may also successfully bound antibodies to the organism that causes Lyme disease as discussed below. One may also successfully attach antibodies to a portion of the bacteria responsible to Lyme disease and quantified the response of this Lyme biosensor. Lyme disease is a tick-borne illness caused by the bacteria *Borrelia burgdorferi*. It is estimated that there are at least 30,000 new cases in the United States each year, although there are likely many more cases that go undetected.

Of the patients diagnosed with Lyme disease, many are originally misdiagnosed due to the non-specific symptoms of the disease and lack of sensitive testing available, particularly for early stages of the infection. Late detection of Lyme disease can lead to further complications including permanent neurological disorders. Using flagellar antigen from the *Borrelia* bacteria as the target protein and a commercially available antibody with a high affinity for this antigen, the demonstrated effectiveness of a carbon nanotube-based sensor for Lyme disease was demonstrated.

In one particular embodiment, the present disclosure presents devices. The devices include a semiconductor and a protein coupled to the semiconductor with a linkage comprising a cysteine such that the protein is in electronic communication with the semiconductor. The semiconductor used in these and other embodiments described herein may be a carbon nanotube. Other suitable semiconductors include elements found in Group IV, e.g., silicon and germanium. Compounds that include elements in Groups III and V, or Groups II and VI, or groups IV and VI are also suitable, as well as ternary compounds and alloys. Germanium, gallium arsenide, and silicon carbide are suitable as well. The semiconductor may include one or more dopants, e.g., boron or phosphorus. Crystalline solids are suitable forms for the semiconductor, but amorphous and liquid semiconductors are also suitable. These may include hydrogenated amorphous silicon and mixtures of arsenic, selenium and tellurium in a variety of proportions. Organic semiconductors, that is, organic materials with properties resembling conventional semiconductors, are also suitable.

The devices may include a device capable of detecting a change in an electronic characteristic of the protein related to an interaction between the protein and an analyte complementary to the protein. In one particular embodiment, the protein comprises an antibody to Lyme flagellar protein.

FIG. 8 shows electronic data taken after each step of the chemistry used to attach the antibody to Lyme flagellar protein to the nanotube, as well as the response of the NT biosensor upon exposure to the antigen, Lyme flagellar protein. Changes in the electrical characteristics were measured using conventional electronic instrumentation operated under computer control. Specifically, the set up included a National Instrument PCI-6722 DAQ board to apply the bias voltage and various values of gate voltage. A Keithley 6485 Picoammeter was used to measure current, providing a full I-Vg curve. Similar to osteopontin, there is a characteristic change in the electrical properties of the NTFET when the sensor is exposed to its target analyte. In FIG. 8, there is a clear shift to the left of approximately 2 V in the turnoff voltage following antigen exposure. This is due to a change in the electrostatic gating environment around the nanotube as the antigen is bound.

As the antigen concentration is varied, the response of the sensor (the shift in the turnoff voltage) varies with the concentration. The data is well represented by Hill-Langmuir thermodynamics.

Figure 9:
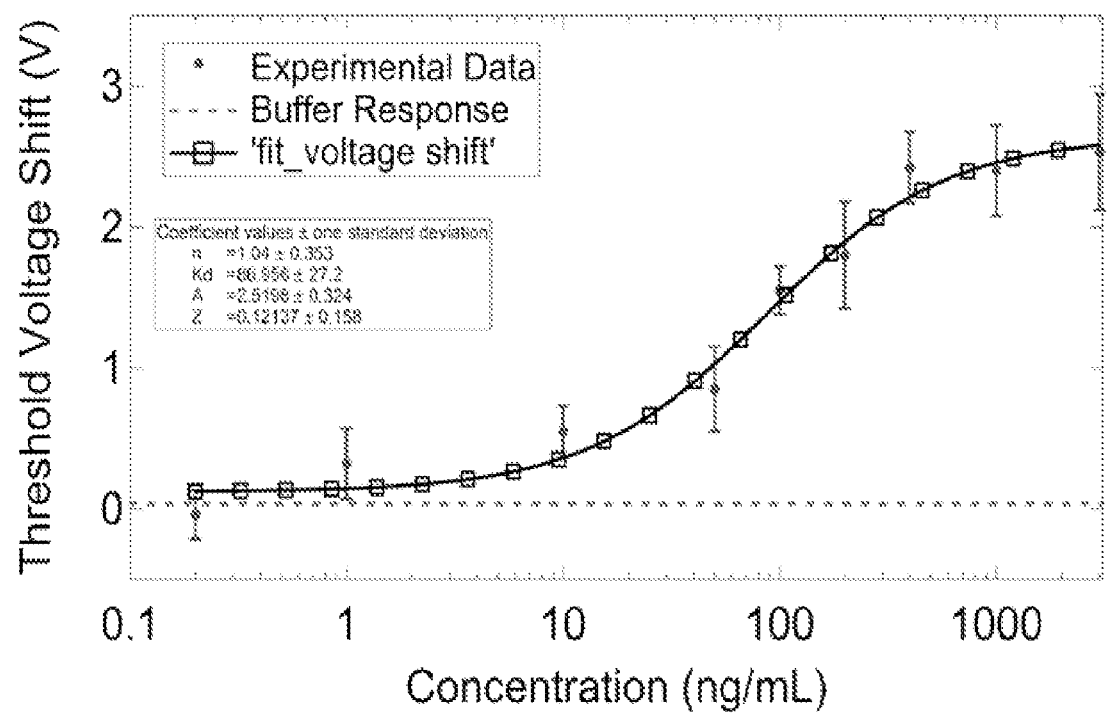
FIG. 9 illustrates a response vs. concentration of Lyme flagellar antigen for functionalized CNTFET biosensors. Fit comes from adapted Hill-Langmuir equation governing equilibrium thermodynamics.

This biosensor can detect Lyme antigen in the clinically relevant regime, with a detection limit below 10 ng/mL (FIG. 9). This is a significant improvement over existing tests for Lyme disease. Additionally, the Hill-Langmuir fit gives information about the dynamics of the system. Binding of the antigen is non-cooperative, meaning one antigen binding to a site on the antibody does not affect the binding of other antigen on other sites. The concentration at which half of binding sites are occupies is approximately 87 ng/mL. The response saturates at a shift of 2.5 V to the left. Lastly, the buffer response and thus minimal response of the sensor are statistically indistinguishable from zero, meaning zero antigen present results in a shift of 0 V.

Summary

Carbon nanotube-protein sensors are disclosed. One specific embodiment is a label-free, all-electronic biosensor for osteopontin (OPN, a protein biomarker associated with prostate cancer) that consists of a genetically engineered single chain variable fragment (scFv) protein antibody with high binding affinity for OPN chemically bonded to a carbon nanotube field-effect transistor (CNTFET) that is used to read out antigen-antibody binding. The biosensor exhibits extremely high sensitivity and selectivity. A chemical functionalization procedure based on a carboxylateddiazonium salt is used to covalently attach the scFv to the carbon nanotube, as confirmed by atomic force microscopy and electronic measurements, while the activity of the biological binding site for OPN and the high quality electronic characteristics of the CNTtranssitor are both preserved. Electronic transport measurements indicate that the functionalized carbon nanotube transistor shows an electrical response associated with binding of OPN to the complementary scFv antibody.

A concentration-dependent increase in the source drain current is observed, with a detection limit of 1 pg/mL, a factor of 1000 superior to the ELISA method. These devices exhibit excellent selectivity for OPN over other proteins and are capable of detecting OPN in a background of concentrated bovine serum albumin protein without loss of signal. The procedures developed here are applicable to any protein or engineered antibody containing an accessible amine group; with modification to incorporate Ni-nitrilotriacetic acid (Ni-NTA) chemistry, they can also be applied to recombinant proteins expressed with a histidine tag, as is commonly done to simplify protein purification. Potential applications include but are not limited to bio/chemical sensors for complementary proteins or vapor phase analytes where the CNTFET/protein hybrid structure provides both chemical recognition and all-electronic readout. Carbon nanotube transistors chemically functionalized in this manner are sensitive to target proteins at 1000× lower concentrations than standard ELISA immunoassays.

To summarize the advantages of nanotubes in biosensors:
1) All electronic readout makes for rapid detection.
2) The inherently low noise in a carbon nanotube transistor provides excellent signal to noise ratio and hence a lower detection limit than conventional techniques.
3) Standardized sensor response across nanotube devices despite variation in nanotube diameters and chiralities.
4) The disclosed functionalization scheme can be adapted for label-free detection of any protein in a single-step process (i.e., no need for a "sandwich" assay or similarly complex procedure) by creating a nanotube transistor functionalized with an antibody (complementary protein) to the target.

REFERENCES

A number of references are provided below. Each reference is incorporated herein by reference in its entirety for any and all purposes.

What is claimed:
1. A device, comprising:
a semiconductor comprising a carbon nanotube;
an antibody that comprises a cysteine,
the antibody coupled to the semiconductor via a linkage such that the antibody is in electronic communication with the semiconductor; and
a detector device capable of detecting a change in an electronic characteristic of the antibody related to an interaction between the antibody and an analyte complementary to the antibody,
wherein the linkage comprises benzoate, a disulfide bond, and the cysteine of the antibody.
2. The device of claim 1, wherein the carbon nanotube comprises a single-wall carbon nanotube.
3. The device of claim 1, wherein the carbon nanotube comprises a multiwall carbon nanotube.
4. The device of claim 1, wherein the antibody comprises an antibody complementary to osteopontin.
5. The device of claim 1, wherein the antibody is coupled to the semiconductor by a covalent bond.
6. The device of claim 5, wherein the antibody is coupled to the semiconductor by an amide bond.
7. The device of claim 1, wherein the antibody comprises a single chain variable fragment.
8. The device of claim 1, wherein the antibody is an anti-HER2 4D5 antibody.
9. A method of fabricating a sensor, comprising:
coupling an antibody comprising a cysteine to a semiconductor that comprises a carbon nanotube,
the coupling being effected via a linkage that comprises benzoate, a disulfide bond, and the cysteine of the antibody, and
the coupling placing the antibody into electronic communication with the semiconductor and with a detector device capable of detecting a change in an electronic characteristic of the antibody related to an interaction between the antibody and an analyte complementary to the antibody.
10. The method of claim 9, wherein the antibody is maintained in essentially its natural configuration following coupling to the semiconductor.
11. The method of claim 9, further comprising displacing a leaving group coupled to the semiconductor with a nucleo- phile group of the antibody so as to form a bond that places the antibody in electronic communication with the semiconductor.

12. The method of claim 11, wherein the leaving group comprises N-Hydroxysuccinimide and the nucleophile group comprises an amine group.

13. A method of assaying a sample, comprising:
    contacting a sample with the device of claim 1; and
    measuring a first electronic characteristic of the device when the device is contacted with the sample.

14. The method of claim 13, further comprising comparing the first electronic characteristic of the device to a corresponding electronic characteristic measured when the device is exposed to a control, a known analyte, or both.

15. The method of claim 14, further comprising generating an estimate of the presence of the known analyte in the sample.

16. The method of claim 14, further comprising constructing a library of one or more electronic characteristics of the device that correspond to the device's exposure to the known analyte.

17. The method of claim 14, comprising comparing the first electronic characteristic of the device to the value of that electronic characteristic corresponding to exposing the device to a known or estimated concentration of the known analyte.

18. The method of claim 14, further comprising generating an estimate of the concentration of the known analyte in the sample.

19. The method of claim 14, further comprising constructing a library of one or more electronic characteristics of the device that correspond to the device's exposure to one or more concentration levels of the known analyte.

20. The method of claim 13, wherein the electronic characteristic comprises conductivity.

* * * * *

UNITED STATES PATENT AND TRADEMARK OFFICE
CERTIFICATE OF CORRECTION

PATENT NO. : 10,983,117 B2  
APPLICATION NO. : 14/241671  
DATED : April 20, 2021  
INVENTOR(S) : Johnson, Jr. et al.

Page 1 of 1

It is certified that error appears in the above-identified patent and that said Letters Patent is hereby corrected as shown below:

In the Specification

Column 2, Line 45, Replace, "of the Hill fit." with -- of the Hill fit; --

Figure 7:
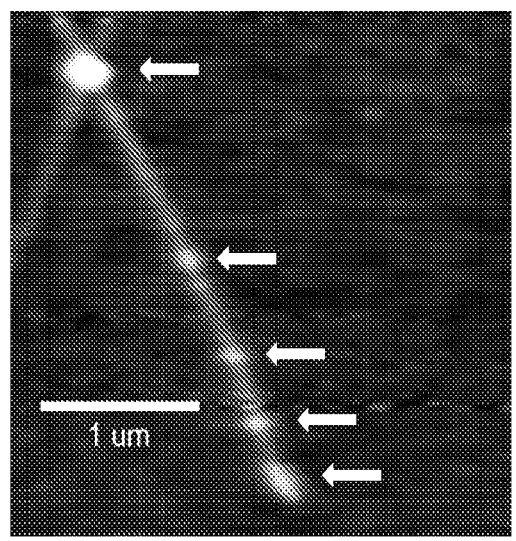
FIG. 7 illustrates successfully attachment of a anti-HER2 4D5 ScFv as confirmed by atomic force microscopy.

Column 2, Line 49, Replace, "FIG. 7 illustrates successfully attachment of a anti-HER2" with -- FIG. 7 illustrates successfully attachment of an anti-HER2 --

Column 5, Line 37, Replace, "Further disclosed are methods" with -- Further, disclosed are methods --

Column 9, Line 27, Replace, "half of binding sites are occupies is approximately" with -- half of binding sites are occupied is approximately --

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*